US00PP10391P

United States Patent [19]

Glicenstein

[11] Patent Number: Plant 10,391

[45] Date of Patent: May 12, 1998

[54] CHRYSANTHEMUM PLANT NAMED 'TRAVIATA'

[75] Inventor: Leon Glicenstein, Salinas, Calif.

[73] Assignee: Yoder Brothers, Inc., Barberton, Ohio

[21] Appl. No.: 702,295

[22] Filed: Aug. 19, 1996

[51] Int. Cl.[6] ..... H01H 5/00

[52] U.S. Cl. ..... Plt./77

[58] Field of Search ..... Plt./77, 82.1

[56] References Cited

U.S. PATENT DOCUMENTS

P.P. 5,009 3/1983 van der Knaap ..... Plt./77

OTHER PUBLICATIONS

UPOV-ROM Plant Variety Database 1997/01. GTI. Cultivar name 'Traviata'.

*Primary Examiner*—Howard J. Locker

*Attorney, Agent, or Firm*—Foley & Lardner

[57] ABSTRACT

A Chrysanthemum plant named Traviata particularly characterized by its flat capitulum form; quilled-decorative capitulum type; white ray floret color; diameter across face of capitulum of 83 to 95 mm when fully opened when grown as a natural spray; when grown as a disbudded cut mum diameter of capitulum is 127 to 140 mm; flowering response in Salinas under normal temperatures is 53 to 58 days after start of short days; flowering response in Bogotá, Colombia is 65 to 74 days after start of short days; plant height is 84 to 102 cm when grown in Salinas with 18 long days prior to start of short days; height is 86 to 97 cm when grown in Bogotá, Colombia with 21 long days prior to start of short days; peduncle length of the first and the fourth laterals at flowering after removing the apical bud is 8 to 10 cm and 13 to 15 cm when grown in Salinas, Calif. and in Bogotá, Colombia; recommended both as a disbudded and a spray cut mum; and uniform flowering in year round flowerings in both Salinas, Calif. and in Bogotá, Colombia.

3 Drawing Sheets

The present invention comprises a new and distinct cultivar of Chrysanthemum, botanically known as *Dendranthema grandiflora*, and referred to by the cultivar name Traviata.

Traviata, identified as 0841 (91-L24004), was originated from a cross made by Leon Glicenstein in a controlled breeding program in Salinas, Calif., in 1991.

The female parent of Traviata was an unnamed seedling identified as 6336 (82-J44004), and described as a flat quilled decorative cut mum with a light pink ray floret color. The female parent was discarded from all programs in April of 1992.

The male parent of Traviata was an unnamed seedling, identified as 1007 (85-245001) and described as a cut mum with a flat decorative flower form with many disc florets and a light pink ray floret color. The male parent was discarded from all programs in January of 1991, after completion of the seed production of described cross.

Traviata was discovered and selecred as one flowering plant within the progeny of the stated cross by Leon Glicenstein in January 1992, in a controlled environment in Salinas, Calif.

The first act of asexual reproduction of Traviata was accomplished when vegetative cuttings were taken from the initial selection in March of 1992 in a controlled environment in Salinas, Calif., by technicians working under supervision of Leon Glicenstein.

Horticultural examination of controlled flowerings of successive plantings has shown that the unique combination of characteristics as herein disclosed for Traviata are firmly fixed and are retained through successive generations of asexual reproduction. Traviata has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and near Bogotá, Colombia, South America under greenhouse conditions which approximate those generally used in commercial greenhouse practice.

The following traits have been repeatedly observed and are determined to be basic characteristics of Traviata, which, in combination, distinguish this Chrysanthemum as a new and distinct cultivar:

1. Flat capitulum form.
2. Quilled-decorative capitulum type.
3. White ray floret color.
4. Diameter across face of capitulum of 83 to 95 mm when fully opened when grown as a natural spray; when grown as a disbudded cut mum diameter of capitulum is 127 to 140 mm.
5. Flowering response in Salinas under normal temperatures is 53 to 58 days after start of short days; flowering response in Bogotá, Colombia is 65 to 74 days after start of short days.
6. Plant height is 84 to 102 cm when grown in Salinas with 18 long days prior to start of short days; height is 86 to 97 cm when grown in Bogotá, Colombia with 21 long days prior to start of short days.
7. Peduncle length of the first and the fourth laterals at flowering after removing the apical bud is 8 to 10 cm and 13 to 15 cm when grown in Salinas, Calif. and in Bogotá, Colombia.
8. Recommended both as a disbudded and a spray cut mum.
9. Uniform flowering in year round flowerings in both Salinas, Calif. and in Bogotá, Colombia.

The accompanying photographic drawings show typical inflorescence and leaf characteristics of Traviata, with the colors being as nearly true as possible with illustrations of this type.

Sheet 1 is a color photograph of Traviata grown as a single stem spray cut mum.

Sheet 2 is a black and white photograph of three views of the inflorescence of Traviata.

Sheet 3 is a black and white photograph showing the upper and under sides of the leaves of Traviata at 3 stages of development (mature, intermediate and immature). In sheets 2 and 3 a measuring tape in centimeters has been added.

Of the commercial cultivars known to the inventor, the most similar in comparison to Traviata is the cultivar Westland Snow disclosed in U.S. Plant Pat. No. 5,009. Reference is made to attached Chart A, which compares certain characteristics of Traviata with the same characteristics of Westland Snow. Similar traits are capitulum form and ray floret color, while the plant height of both cultivars is comparable. Traviata has quilled ray florets, while Westland Snow has spooned ray florets. Traviata has a larger diameter of capitulum when grown as a spray cut mum, a faster flowering response to short days, and shorter peduncles when compared with Westland Snow. Traviata is recommended both as a spray and disbudded cut mum, while Westland Snow is recommended only as a spray cut mum. Traviata shows uniform performance under low night temperatures near Bogotá, Colombia, while Westland Snow does not flower under those temperature conditions, which can be as low as 5 to 8 degrees Celsius. In addition, Westland Snow exhibits many bracts in the flower, while Traviata does not exhibit this trait.

In the following description color references are made to The Royal Horticultural Society Colour Chart. The color values were determined on plant material grown as a single stem spray cut mum in Salinas, Calif. on Jun. 13, 1996.

Classification:

*Botanical.*—*Dendranthema grandiflora* cv Traviata.

*Commercial.*—Flat quilled-decorative spray and disbud cut mum.

Inflorescence

A. Capitulum:

*Form.*—Flat.

*Type.*—Quilled-decorative.

*Diameter across face.*—83 to 95 mm as spray, 127 to 140 mm as disbud when fully opened.

B. Corolla of ray florets:

*Color (general tonality from a distance of three meters)*.—White.

*Color (upper surface).*—155D.

*Color (under surface).*—155D.

*Shape.*—Quilled, straight.

C. Corolla of disc florets:

*Color (mature).*—Closest to 14A.

*Color (immature).*—Closest to 144A.

D. Reproductive organs:

*Androecium.*—Present on disc florets only; no pollen.

*Gynoecium.*—Present on both ray and disc florets.

Plant

A. General appearance:

*Height.*—84 to 102 cm when grown in Salinas with 18 long days prior to start of short days; height is 86 to 97 cm when grown in Bogotá, Colombia with 21 long days prior to start of short days.

B. Foliage:

*Color (upper surface).*—147A.

*Color (under surface).*—147B.

*Shape.*—Long, narrow, lobed and serrated.

CHART A
COMPARISONS MADE OF PLANTS GROWN AS SINGLE STEM SPRAY CUT MUMS IN SALINAS, CALIFORNIA AND IN BOGOTA, COLOMBIA

| CHARACTERISTIC | TRAVIATA | WESTLAND SNOW |
|---|---|---|
| Ray floret color | White | White |
| Capitulum form and type | Flat Quilled-decorative | Flat Spooned-decorative |
| Diameter across face of capitulum | | |
| as spray | 76 to 83 mm | 70 to 76 mm |
| as disbud | 127 to 140 mm | Not available |
| Flowering response | | |
| in Salinas | 53 to 58 days | 55 to 61 days |
| in Bogotá | 65 to 74 days | Not available |
| Plant height in Salinas | 86 to 97 cm | 84 to 102 cm |
| Peduncle length | | |
| 1st lateral | 8 to 10 cm | 10 to 13 cm |
| 4th lateral | 13 to 15 cm | 15 to 20 cm |

What is claimed is:

1. A new and distinct Chrysanthemum plant named Traviata, as described and illustrated.

* * * * *

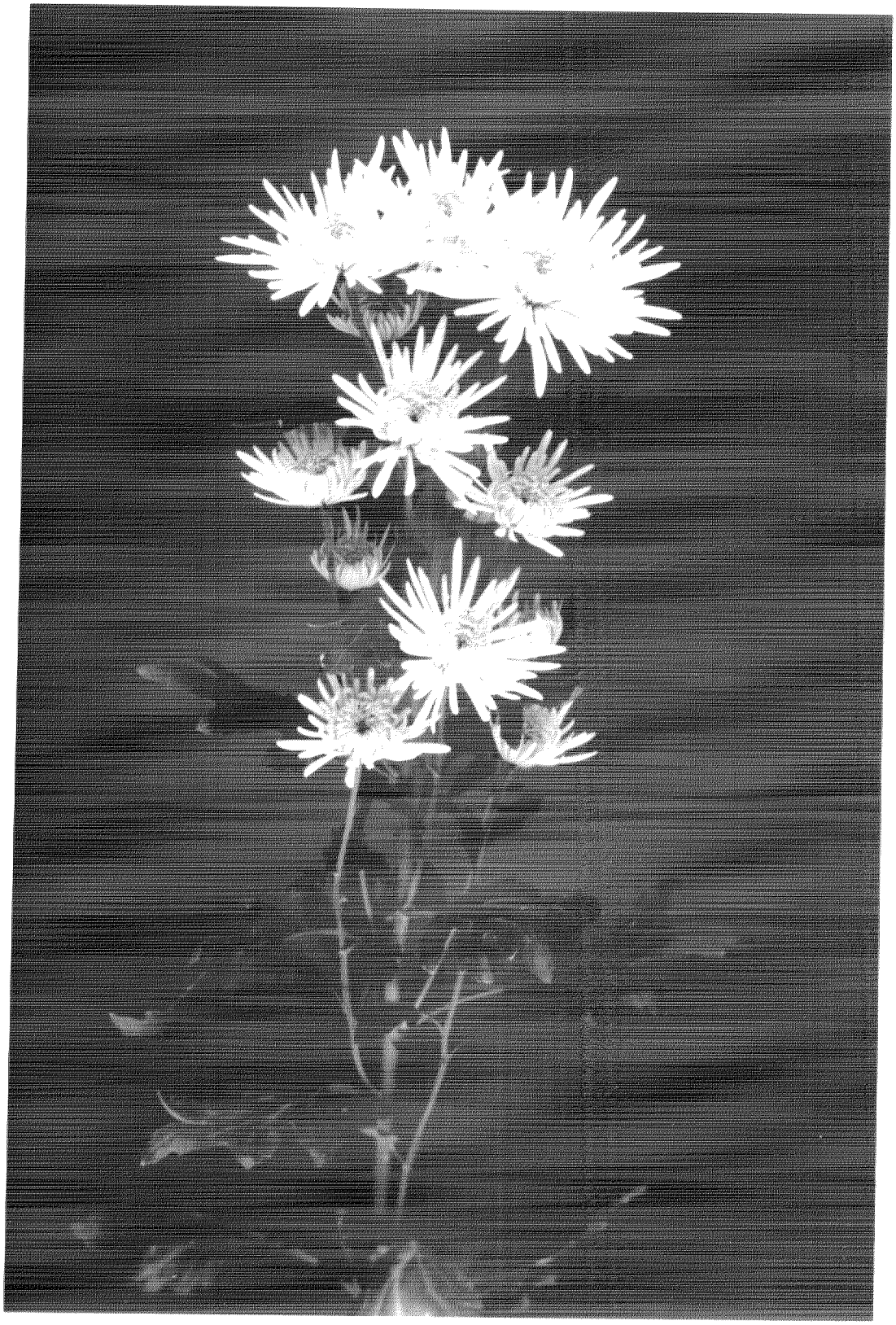

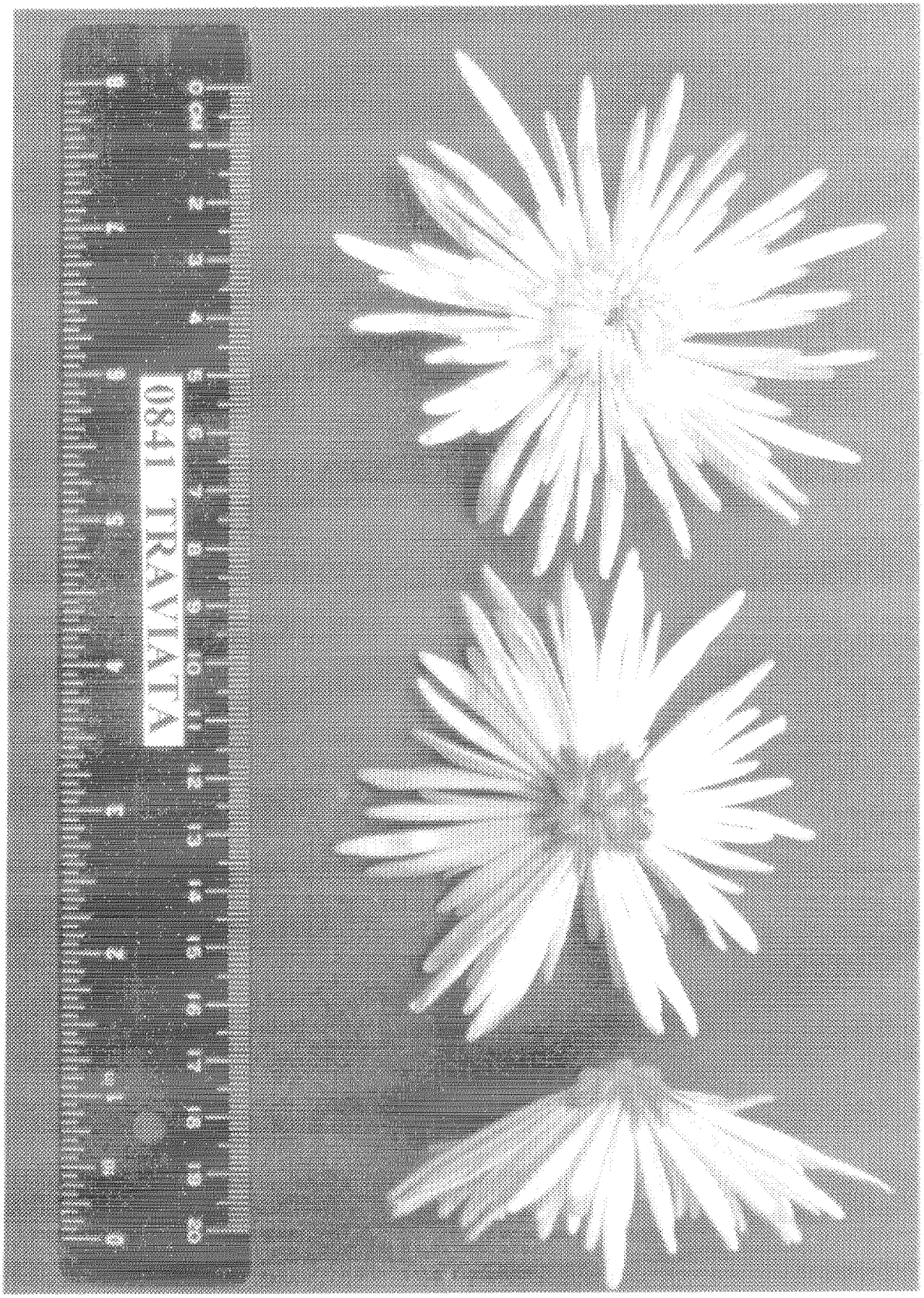
0841 TRAVIATA

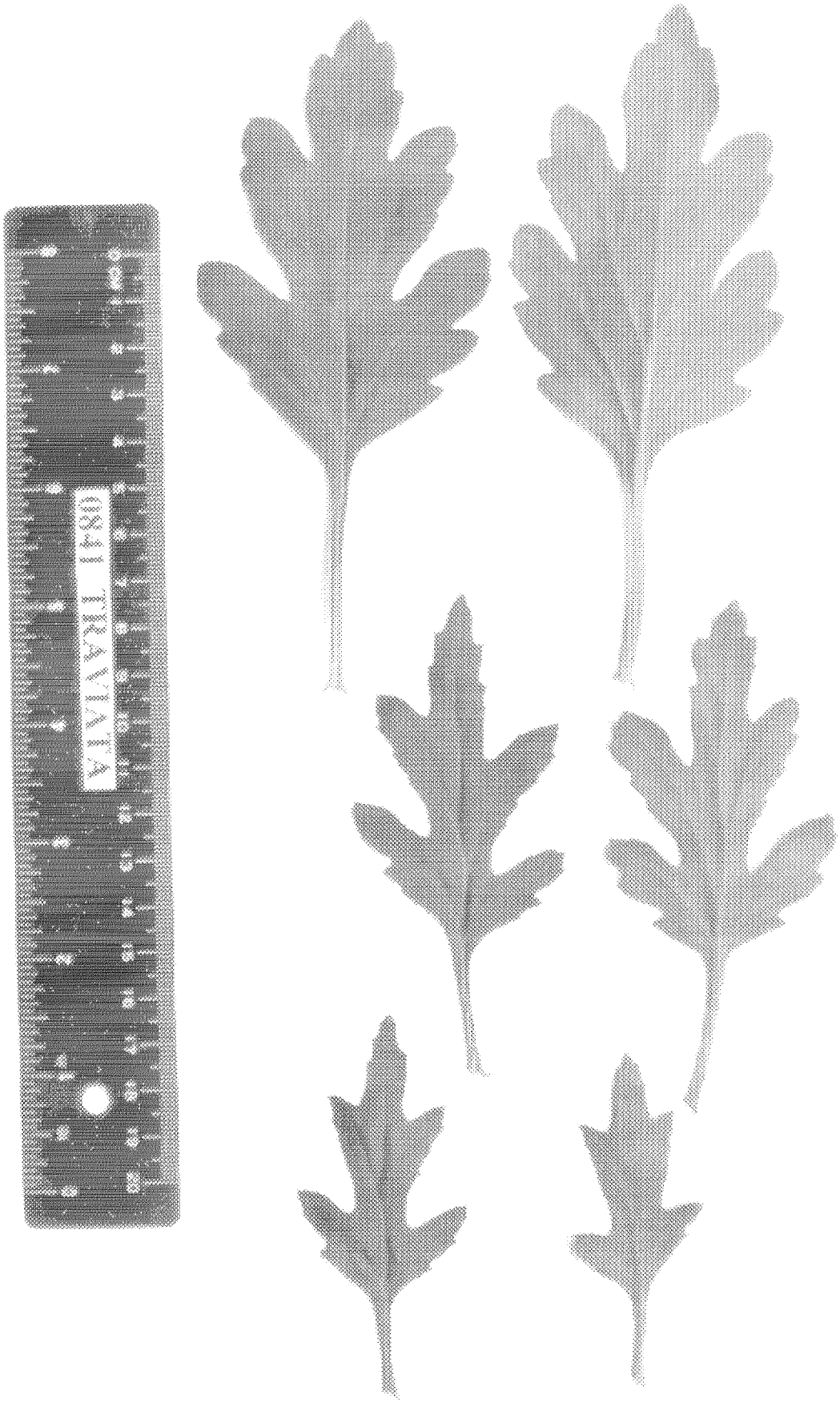
VAVIAVIL 1980